(12) United States Patent
Hirt et al.

(10) Patent No.: US 6,558,397 B2
(45) Date of Patent: May 6, 2003

(54) DEVICE FOR REMOVAL OF CALCULI

(75) Inventors: Joachim Hirt, Constance (DE); Andreas Menne, Meersburg (DE)

(73) Assignee: Ferton Holding S.A. (CH)

( * ) Notice: Subject to any disclaimer, the term of this patent is extended or adjusted under 35 U.S.C. 154(b) by 26 days.

(21) Appl. No.: 09/878,109

(22) Filed: Jun. 8, 2001

(65) Prior Publication Data

US 2002/0010477 A1 Jan. 24, 2002

(30) Foreign Application Priority Data

Jun. 15, 2000 (DE) .......................................... 100 29 581

(51) Int. Cl.[7] .............................................. A61B 17/22
(52) U.S. Cl. ........................................ 606/128; 606/127
(58) Field of Search .............................. 606/127, 128, 606/32, 34, 35, 36, 238, 239

(56) References Cited

U.S. PATENT DOCUMENTS 4,979,952 A  * 12/1990 Kubota et al. ........... 606/127 X
5,160,336 A     11/1992 Favre ........................ 606/128
5,741,272 A  *  4/1998 Kuhne ....................... 606/128
5,836,897 A  * 11/1998 Sakurai et al. .......... 606/128 X
5,868,756 A  *  2/1999 Henry et al. ............... 606/128
6,083,232 A  *  7/2000 Cox .......................... 606/128
6,149,656 A  * 11/2000 Walz et al. ................ 606/128
6,312,434 B1 * 11/2001 Sutrina et al. ............. 606/127

FOREIGN PATENT DOCUMENTS

EP         0421258 B1    11/1994

* cited by examiner

Primary Examiner—Gloria M. Hale
(74) Attorney, Agent, or Firm—Ostrolenk, Faber, Gerb & Soffen, LLP

(57) ABSTRACT

A device for removing calculi by using an intracorporeal lithotripter comprises a single metallic probe or sonotrode which for the fragmentation of calculi is connected with an electrically controlled ultrasonic transducer for generating longitudinal oscillations which alternatively may be switched to the generation of shock or pressure waves by either a pulse wave stimulated oscillation of the metallic probe or sonotrode or by a reversibly driven impact member or projectile which is accommodated by the hollow of a backward tubular extension of the sonotrode.

12 Claims, 1 Drawing Sheet

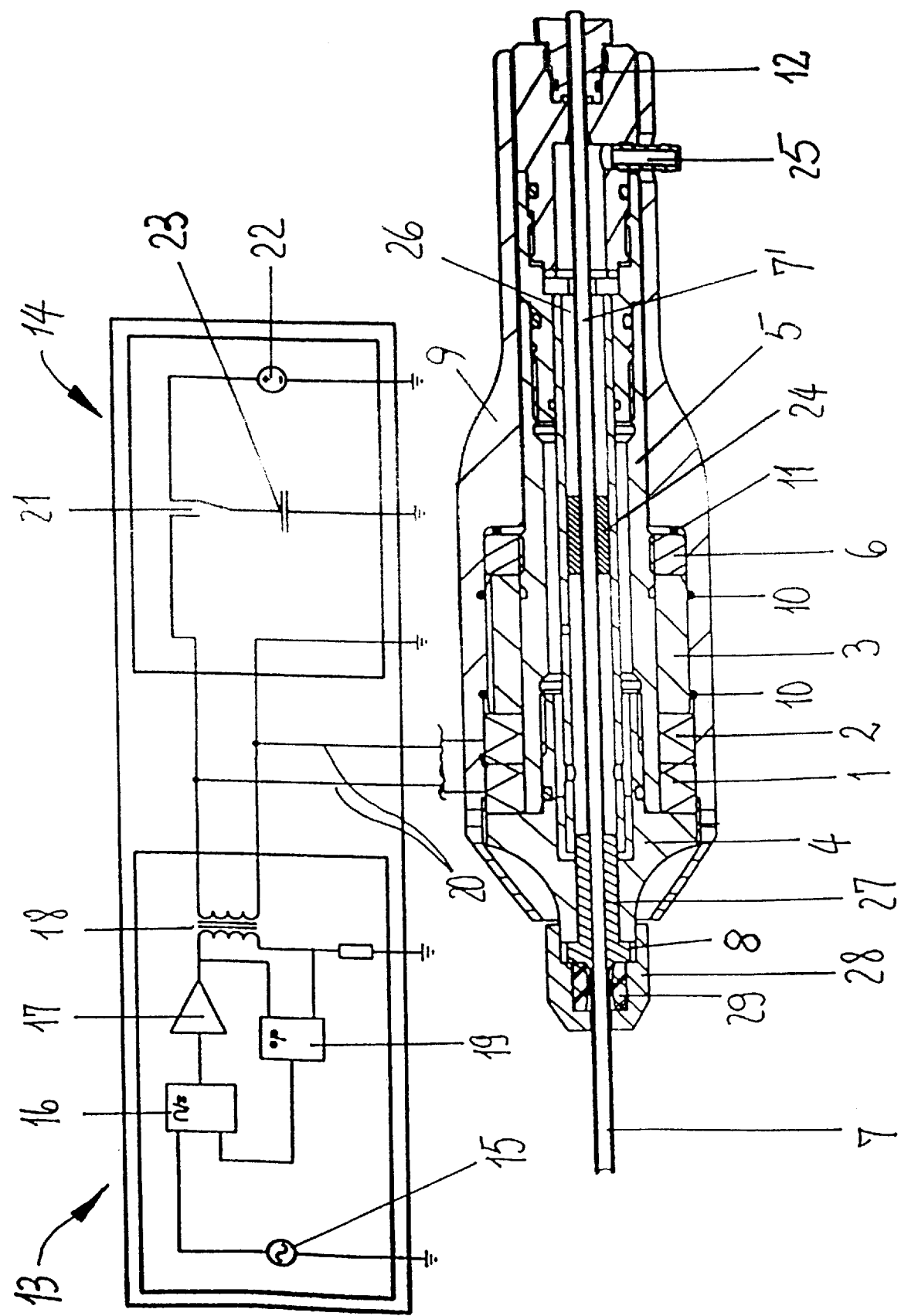

DEVICE FOR REMOVAL OF CALCULI

FIELD OF THE INVENTION

This invention relates to a device for removal of calculi by using an intracorporeal lithotripter.

BACKGROUND OF THE INVENTION

When removing calculi from body hollows it becomes necessary in general to crash first in situ those calculi which although still suitable for allowing a natural exit or drainage exceed a predetermined size. It therefore will be necessary to crash or fragment any overdimensioned calculi and to generate particles of a more or less minute size to thereby allow such minimised particles to being spontaneously removed from the body hollow. The minimisation is carried out by acting on the calculi with compressive and tensional forces which in the field of intracorporeal lithotripsy are exercised with the distal end of a metallic probe serving as a wave guide. Such forces result in a blasting-off of fragments from the surface of a calculus for effecting its crashing. However, when fragmenting calculi in this way, there exists in general the problem of providing suitable energy transport or energy transfer specifically to those calculi which are to be minimised by avoiding at the same time any disturbing and rather dangerous side effects on the human tissue which therefore should not serve as a backing during such a fragmentation of calculi.

The European Patent EP 0 421 285 B1 discloses a device for removal of calculi by using an intracorporeal lithotripter. The device comprises a metallic probe or sonotrode which by means of an electrically controlled ultrasonic transducer generates longitudinal oscillations. When inserted into the operating passage of an endoscope as used for a fragmentation of calculi the distal end of the metallic probe or sonotrode when in contact with the calculi will crash the same by the transfer of those longitudinal oscillations. The ultrasonic transducer is composed of piezoceramic discs which are arranged within a surrounding casing between a reflector and a horn that are fastened to each other. For periodically oscillating the sonotrode the piezoceramic discs are controlled by a circuit arrangement which comprises a voltage-controlled oscillator the output signal of which is supplied to the piezoceramic discs via an output amplifier and an output transmitter. The circuit arrangement comprises a phase comparator for comparing the phases of the output voltage and of the output current of the output transmitter for generating a control voltage of the oscillator. With a device of this kind it will be possible to crash calculi into very fine fragments with a particle size which in general will not create any problems in sucking-off the calculi fragments through an axial hollow of the sonotrode and extending at its proximal end to an interconnected suction duct which is passed through the ultrasonic transducer. Any minimisation of calculi by means of an intracorporeal lithotripter operating with an ultrasonic transducer must be considered, however, as relatively time-consuming since for a careful handling of the lithotripter at the distal end of the tubular sonotrode it will only be allowable to use ultrasonic frequencies of about 20 to 25 kHz with amplitudes of about 50 $\mu$m for avoiding any damages of the human tissue. There will also be exist certain complications with calculi of a harder consistency which will not allow any spontaneous peeling with such frequencies and amplitudes at the tip of the sonotrode. The operational treatment will accordingly either last very long or will even be impossible.

The European Patent EP 0 317 507 B1 discloses a lithotripter comprising a metallic probe the proximal end of which is arranged for being hit periodically by a pneumatically driven impact member or projectile resulting in an impact energy which is transported along the metallic probe as far as to its distal end so that any calculus when contacted with the tip of the probe will be fragmented under the action of shock or pressure waves. Such shock or pressure wave lithotripters which with alternative designs may also be provided with an electric drive for the impact member or projectile are constructed in general as relatively simple units having nevertheless very high efficiencies with the fragmentation of calculi. although it has to be conceded that the handling of such shock or pressure wave lithotripters is still somewhat time-consuming in the context of providing particles that may be spontaneously sucked-off.

SUMMARY OF THE INVENTION

An object of the present invention is to provide a device for removal of calculi by using an intracorporeal lithotripter which will allow a more flexible fragmentation of calculi under consideration of the advantages and the disadvantages of the presently known methods when using lithotripters of the kind as above described.

In accordance with the present invention a device for removal of calculi by using an intracorporeal lithotripter of the kind as referred above is provided which is characterised by the features of the claims.

The present invention offers the possibility for using the device for removing calculi by a combination of the operating principles of a known ultrasonic wave lithotripter with those of a known shock wave lithotripter whereby any change-over between such two operating principles may be effected by simple measures. The device according to the present invention is in particular advantageous by offering the possibility for exercising both operating principles by the use of a single metallic probe or sonotrode which when designed with a tubular form will also allow to suck-off all of the particles resulting from a fragmentation of calculi by a contact with the tip of the metallic probe or sonotrode. The fragmentation of calculi may therefore be conducted very effectively also by the incorporation of the possibility for a change-over between a periodic and a pulse wave stimulated oscillation stimulation as imparted to one and the same metallic probe or sonotrode by a coupling of the ultrasonic transducer with two respectively separate circuit systems that are adapted for controlling such different operational modes for the fragmentation of calculi.

Other objects, features and advantages of the present invention will become apparent from reading the following description of a preferred embodiment of a device according to the present invention.

BRIEF DESCRIPTION OF THE DRAWINGS

The invention will now be described by way of example, with reference to the accompanying drawing which shows a sectional view of the device together with a diagram showing the circuitry of its ultrasonic transducer.

DETAILED DESCRIPTION OF THE PREFERRED EMBODIMENT

The device for removal of calculi as shown in the drawing comprises an electrically controlled ultrasonic transducer which is designed as a piezoelectric transducer having two piezoceramic discs 1 and 2 arranged between a reflector 3 and a horn 4. The arrangement comprising these elements of the ultrasonic transducer are fixedly interconnected by means of a hollow fastening stud bolt 5 which is axially passed through the two ceramic discs 1, 2 and the reflector 3 for being tightened by a screw nut 6 which holds this arrangement. A tubular metallic probe or sonotrode 7 is releasably connected with the horn 4 by a screw portion 8 so that the hollow of the fastening stud bolt 5 is axially extended into the hollow of the metallic probe or sonotrode 7.

The ultrasonic transducer comprising those elements as mentioned before and held together by the fastening stud bolt 5 is arranged within a casing 9 which is formed with two parts. The partition plane of the casing is located in the vicinity of the horn 4 so that the fastening stud bolt 5 allows at the same time an elastic fastening of the ultrasonic transducer also with respect to this casing via elastic supporting means in the form of O-rings 10 and of a packing 11 which are supporting the ultrasonic transducer on the casing 9. The hollow fastening stud bolt 5 is connected at its outer end with a suction duct connection 12 so that any fragments of calculi which will be generated with the tip end of the metallic probe or sonotrode 7 may be sucked-off via the hollow of the metallic probe or sonotrode and the axially aligned hollow of the fastening stud bolt 5.

The two piezoceramic discs 1,2 are coupled with a first circuit system 13 for stimulating periodic oscillations of the metallic probe or sonotrode 7 and with a second circuit system 14 for stimulating a pulse wave oscillation of one and the same metallic probe or sonotrode. The first circuit system 13 comprises a voltage-controlled oscillator 15 which is connected via a voltage-frequency transducer 16 and an interconnected output amplifier 17 to an impedance transformer 18. The impedance transformer 18 is coupled with the voltage-frequency transducer 16 via a phase comparator 19 which is arranged for comparing the phases of the output voltage and the output current of the impedance transformer 18 to thereby generate a control voltage for the oscillator 15. The first circuit system 13 therefore generates with its output signal a periodic oscillation stimulation of the metallic probe or sonotrode 7 via connecting lines 20 leading to the two piezoceramic discs.

The two piezoceramic discs 1, 2 are on the other side also connected with the second circuit system 14 which is arranged for stimulating a pulse wave oscillation of the metallic probe or sonotrode 7. The second circuit system 14 comprises a voltage source 22 and a capacitor 23 which in a first control position of an interconnected change-over switch 21 is loaded by the voltage source 22. When switched to a second control position of the change-over switch 21 the capacitor 23 will then be discharged for stimulating the metallic probe or sonotrode with a single shock or pressure wave by means of the two piezoceramic discs 1, 2. Since the piezoelectric transducer will be supplied with a much higher power by the output signal of the second circuit system 14 in comparison with the output signal as supplied by the first circuit system 13 the two piezoceramic discs 1, 2 will be instantaneously expanded by this much higher power which therefore results in the generation of only a singular shock or pressure wave in the metallic probe or sonotrode 7 and accordingly only in a corresponding single pressure pulse which will be transferred by the distal end of the sonotrode to any calculus which is being kept in contact with this distal end when the fragmentation of calculi proceeds.

For obtaining optimum results for such a pulse wave stimulated oscillation of the metallic probe or sonotrode 7 the horn 4 of the ultrasonic transducer as well as the sonotrode 7 should comprise a material of substantially the same acoustic impedance. As preferred materials high-grade steel or titanium should be used. The horn 4 should be further provided with an enveloping surface which tapers in the axial direction substantially to the cross-section of the screw portion 8 being provided for a screw connection also with a screw cap 28 which by means of an attenuation element 29 is connected with.the metallic probe or sonotrode 7. It is to be understood that the elastic means 10, 11 which are provided for supporting the ultrasonic transducer on the surrounding casing 9 should also be formed such as to provide optimum operating conditions both for the periodic and the pulse wave stimulated oscillation of the metallic probe or sonotrode.

The device is further designed such as to also allow a change-over to the drive of an impact member or projectile 24 which is accommodated in the hollow of the fastening stud bolt 5. The drive of this impact member or projectile 24 may be either hydraulically or electrically controlled or may be of a pneumatic design as considered for the presently preferred embodiment of the device according to the present invention and shown in the drawing. The device is therefore further provided with a pressure duct inlet 25 which is connected to the hollow 26 of the fastening stud bolt 5. Further details of this pneumatic drive for the reciprocating movement of the impact member or projectile 24 will not be described since in this respect reference may be made to the prior art design as disclosed in EP 0 317 507 B1. The preferred embodiment of the device according to the present invention differs however, over the known design more or less only in the detail that the impact member or projectile 24 is axially guided via its circumferential surface on the wall of the surrounding hollow 26 of the fastening stud bolt 5 and in addition by a backward extension 7' of the hollow metallic probe or sonotrode 7 by means of a centering bore of the projectile. The impact member or projectile 24 is arranged for exercising an impact force against a mass body 27 which is formed with a metallic bush which is located at the transition portion of the metallic probe or sonotrode 7 and its backward extension 7'. The arrangement is such that the mass body 27 is provided with a screw connection with the horn 4 as provided by the screw portion 8 which also has a screw connection with the screw cap 28 that is connected via the attenuation element 29 with the sonotrode. It is to be under stood that the mass body could alternatively be also designed with such an arrangement inside of the hollow 26 of the fastening stud bolt 5 as described in U.S. Pat. No. 5,868,756 which therefore is incorporated here for a further reference.

We claim:

1. A device for removing calculi by using an intracorporeal lithotripter, comprising:
    a metallic probe or sonotrode serving as a wave guide and being inserted into an operating passage of an endoscope for a fragmentation of calculi via a distal end of said metallic probe or sonotrode;
    an electrically controlled ultrasonic transducer for generating longitudinal oscillations, for being transferred to said metallic probe or sonotrode;
    the electrically controlled oscillations of said metallic probe or sonotrode as electrically controlled by said ultrasonic transducer being switchable to the generation of shock or pressure waves in the metallic probe or sonotrode.

2. The device according to claim 1, wherein the electrical control of said ultrasonic transducer is switchable between a periodically stimulated oscillation and a pulse wave stimulated oscillation of said metallic probe or sonotrode.

3. The device according to claim 1, wherein two separate first and second circuit systems are provided for controlling said periodic and said pulse wave stimulated oscillations, respectively, of said metallic probe or sonotrode, wherein a first circuit system for controlling the periodic oscillation of the metallic probe or sonotrode comprises a voltage-controlled oscillator which is connected via a voltage-frequency transducer and an interconnected output amplifier to an impedance transformer, and a phase comparator which is arranged for comparing the phases of the output voltage and the output current of the impedance transformer to thereby generate a control voltage for the oscillator;

a second circuit system for controlling the pulse wave stimulated oscillation of the metallic probe or sonotrode comprises a voltage source and a capacitor being interconnected via a change-over switch, the arrangement being such that when the ultrasonic transducer is coupled via said change-over switch to the second circuit system said shock or pressure waves will be generated in the metallic probe or sonotrode.

4. The device according to claim 3, wherein said capacitor is loaded in a first control position of said change-over switch and when switched to a second control position is coupled with said ultrasonic transducer, the capacitor being discharged in the second control position for stimulating said metallic probe or sonotrode with a single shock or pressure wave.

5. The device according to claim 1, wherein said ultrasonic transducer comprises at least one piezoceramic disc which is arranged between a reflector and a horn that carries said metallic probe or sonotrode, the arrangement being fixedly interconnected by means of a hollow fastening stud bolt the hollow of which accommodates a reversibly driven impact member or projectile which is arranged for exercising an impact force against a mass body of said metallic probe or sonotrode to thereby generate said shock or pressure waves.

6. The device according to claim 5, wherein said metallic probe or sonotrode is releasably connected with said horn of the ultrasonic transducer by means of a screw cap, the metallic probe or sonotrode having a head portion which forms said mass body and which is supported on said screw cap by means of an attenuation element, the attenuation element being arranged for allowing a non-positive connection between the horn and the metallic probe or sonotrode for attenuating its oscillations.

7. The device according to claim 5, wherein said metallic probe or sonotrode is tubular and is provided with a backwardly extended elongation which protrudes axially into the hollow of said fastening stud bolt and extends to a suction duct connection.

8. The device according to claim 5, wherein said impact member or projectile is provided with a centering bore for being axially guided by said backward elongation of said metallic probe or sonotrode and by the surrounding wall of the hollow of said fastening stud bolt.

9. The device according to claim 5, wherein the hollow of said fastening stud bolt is provided with a pressure duct inlet of a pneumatic drive by which said impact member or projectile is reversibly driven.

10. The device according to claim 5, wherein said arrangement comprising said ultrasonic transducer and said fastening stud bolt is supported on a surrounding casing by elastic supporting means.

11. The device according to claim 5, wherein said horn has an enveloping surface which tapers in the axial direction substantially to the cross-section of a screw portion which is provided for a screw connection with said screw cap.

12. The device according to claim 5, wherein said metallic probe or sonotrode and said horn comprise a material of substantially the same acoustic impedance such as preferably high-grade steel or titanium.

* * * * *